United States Patent [19]

Harsy

[11] Patent Number: 4,924,029
[45] Date of Patent: May 8, 1990

[54] REDUCTION OF NITROALIPHATICS VIA HOMOGENEOUS CATALYSIS

[75] Inventor: Stephen G. Harsy, Mt. Airy, Md.

[73] Assignee: W. R. Grace & Co.-Conn., New York, N.Y.

[21] Appl. No.: 210,944

[22] Filed: Jun. 24, 1988

[51] Int. Cl.$^5$ .............................................. C07C 85/11
[52] U.S. Cl. ..................................... 564/418; 564/495
[58] Field of Search ................................ 564/418, 495

[56] References Cited

U.S. PATENT DOCUMENTS

| | | | |
|---|---|---|---|
| 2,587,572 | 2/1952 | Tryon | 564/495 |
| 3,534,112 | 10/1970 | Tindall | 564/495 |
| 3,546,298 | 12/1970 | Tindall | 564/495 |
| 3,564,057 | 2/1971 | Tindall | 564/495 |
| 3,564,062 | 2/1971 | Tindall | 564/495 |
| 3,651,144 | 3/1972 | Tindall | 564/495 |
| 3,736,265 | 5/1973 | Suggitt | 564/495 |
| 3,739,027 | 6/1973 | Gates | 564/495 |
| 3,832,401 | 8/1974 | Knifton et al. | 564/418 |
| 3,845,130 | 10/1974 | Suggitt | 564/495 |
| 3,917,706 | 11/1975 | Hudson et al. | 564/495 |
| 3,944,615 | 3/1976 | Iqbal | 564/418 |
| 4,067,905 | 1/1978 | Adrian et al. | 564/495 |
| 4,157,445 | 6/1979 | Fitton et al. | 564/418 |
| 4,204,997 | 5/1980 | Hobbs et al. | 502/162 |
| 4,448,999 | 5/1984 | Thewalt et al. | 564/495 |

FOREIGN PATENT DOCUMENTS 0083332 12/1982 European Pat. Off. .

OTHER PUBLICATIONS

"Homogeneous Catalyzed Reduction of Nitro Compounds. III. Synthesis of Aliphatic Amines," by J. F. Knifton, J. Org. Chem. 40, 519.

*Primary Examiner*—Glennon H. Hollrah
*Assistant Examiner*—Susan P. Treanor
*Attorney, Agent, or Firm*—Howard J. Troffkin

[57] ABSTRACT

A homogeneous catalytic hydrogenation of nitroalcohols to amino alcohols is described in which a solution of nitroalcohol is contacted with hydrogen under low temperatures and in the presence of a soluble complex of an organometallic compound of Rh, Ir, Pt or Pd and an organophosphine.

6 Claims, No Drawings

REDUCTION OF NITROALIPHATICS VIA HOMOGENEOUS CATALYSIS

BACKGROUND OF THE INVENTION

The present invention is directed to a process of hydrogenating nitroalcohols to form aminoalcohols using a homogeneous catalyst system.

The products formed by the present process, aminoalcohols, are known to be useful as disinfectants, lubricating oil additives, textile resin catalysts, buffers and as intermediates in the production of pharmaceutical agents.

It has been known that nitro hydroxyl compounds can be hydrogenated to provide the corresponding amino hydroxyl compounds under certain conditions. In general, the present processes provide for the contacting of a nitroalcohol with a hydrogenation catalyst in a liquid medium. The materials are contained in a suitable apparatus to which hydrogen gas is introduced under pressure. The hydrogenation catalysts deemed suitable for this process are heterogeneous formulations of a Group VII-B or VIII metal. Such materials include porous or spongy metal material such as spongy nickel or Raney nickel or a supported metal or metal compound wherein the catalytically active Group VII-B or VIII metal forms a minor component of the catalyst and is distributed on a variety of inert support materials. Heterogeneous catalysts in many instances provide acceptable initial activity and mechanical strength but are known to rapidly loose their activity and, in the case of supported materials, to soften and disintegrate thereby making heterogeneous catalyst systems unattractive for commercial size operations.

Homogeneous catalyst systems have been used in the reduction of nitroparaffins (see J. F. Knifton article in J. Org. Chem. 40 519–20). In the reduction of nitro compounds, Knifton teaches that a strong base must be present to activate the catalyst complex or the catalyst activity would be so low as to require high catalyst loading and, even then, to achieve low yields. The use of a homogeneous catalyst to reduce nitroparaffins and nitroaromatics has also been reported by Asish Bose et al. in Chemistry & Industry 199 (1987). Bose et al. teach that this homogeneous catalyst system requires the use of a coordination compound. It is well known that hydroxyl groups will decompose and in certain instances cause the nitro alcohol substrate to disintegrate when in the presence of base or coordination compounds as are taught necessary. The systems of Knifton and Bose et al. are, therefore, not applicable to reduction of nitro hydroxyl compounds to which the present invention is directed.

A homogeneous catalyst system is desired to provide effective reduction of nitroalcohols to aminoalcohols.

SUMMARY OF THE INVENTION

The present invention is directed to specific catalyst systems which are capable of providing an effective process for a homogeneous phase reduction of nitroalcohols to amino alcohols. A solution of nitroalcohol is contacted with a soluble organometallic phosphine complex formed from a soluble organometallic compound of a metal selected from rhodium, iridium, platinum or palladium and a soluble organophosphine compound. The solution is subjected to hydrogen pressure at mildly elevated temperatures to cause formation of aminoalcohol product.

DETAILED DESCRIPTION OF THE INVENTION

The invention described in detail hereinbelow is directed to the reduction of nitroalcohols to aminoalcohols using a homogeneous catalyst system.

The nitroalcohols which can be effectively reduced according to the present process are compounds represented by the formula:

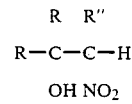

wherein each R, R' and R" independently represents a hydrogen, alkyl, or substituted alkyl. The substitution group can be selected from hydroxy, halogen, primary, secondary or tertiary amino, or aryl group. It is noted that the nitro alcohol capable of being effectively reduced by the present process contains a hydroxyl and a nitro group on adjacent carbon atoms and that these carbons are covalently bonded by an aliphatic single bond. Such compounds are normally unstable under reductive hydrogenation when in the presence of a strong base or a coordination compound. For example, it is known that alpha-nitro hydroxy compounds are formed from the corresponding carbonyl compound and nitro compound and that strong base causes the nitro hydroxy compound to decompose back to the starting materials.

The present process requires the utilization of an inert solvent which can be selected from certain organic solvents as fully described below or miscible mixtures of said solvents. The solvent selected must be capable of being liquid under the reaction conditions and solubilizing the nitroalcohol reactant and the catalyst complex described below to provide a substantially homogeneous phase reaction. The organic solvents can be selected from alcohols such as $C_1$–$C_5$ alkanol as for example methanol, ethanol, propanol, butanol and the like; or alkanediols such as ethylene glycol, 1,3-propanediol, 1,4-butanediol and the like. Ethers may be useful solvents and include dialkyl ethers or cyclic ethers, such as dimethyl ether, diethyl ether diisopropyl ether, dioxane, tetrahydrofuran and the like. Another class of organic compounds useful as solvents in the present process includes aromatic hydrocarbons such as benzene, toluene and the like. The solvent should be free of carbonyl, halogen, amide, or carboxyl group containing compounds. The solvent may be formed from a mixture of the above compounds to provide a homogeneous phase medium. The preferred solvents are $C_1$–$C_3$ alkanols, benzene lower dialkyl ethers and mixtures thereof, in particular, mixtures of an alkanol and benzene.

The present process requires the presence of a catalyst material which is capable of being soluble in the reaction solution. The catalyst is an organometallic phosphine complex either preformed or formed in situ from soluble organometallic compound of a metal selected from rhodium, iridium, platinum or palladium and a soluble organophosphine. Examples of organometallic compounds suitable for forming the complex include rhodium norbornadiene dihalides [RhCl$_2$(NBD)$_2$], iridium iridium norbornadiene dihalides [IrCl$_2$(NBD)$_2$], iridium cyclooctadiene dihalide [IrCl$_2$(COD)$_2$], rhodium carbonyl halides [Rh$_2$(CO)$_4$Cl$_2$], platinum or palladium dihalide ligand compounds where the ligand can be, for example, benzonitrile, acetonitrile and the like. In addition platinum and palladium salts, such as halides may be used as the precursor compound in forming the organometallic phosphine complex.

The organo phosphine useful in providing the complex required in the present process can be represented by PZ$_3$ wherein each Z can separately represent an organic radical preferably selected from a phenyl or C$_1$–C$_{12}$ (preferably C$_1$–C$_6$) alkyl group. In addition, useful organo phosphines include diphosphines represented by Z$_2$P—Y—PZ$_2$ wherein each Z is separately selected from the groups defined above and Y represents an alkyl or aryl group or an organo metallic bridging group (such as a ferrocene group and the like) such that the Y group has two phosphorous atoms attached thereto. Examples include triphenylphosphine, trimethylphosphine, dimethylphenylphosphine, tricyclohexylphosphine alpha-[2,1'-bis(diphenylphosphino)-ferrocenyl]ethanol, 2,2'-bis(diphenylphosphino)-1,1'-binaphthyl, 2,3-bis(diphenylphosphino)butane, 2,2-dimethyl-4,5-bis(diphenylphosphinomethyl)-1,3-dioxolane, alpha[2-(diphenylphosphino)-ferrocenyl]ethyldimethylamine, 1,2-bis(diphenylphosphino) propane, and the like.

The organometallic and the organophosphine are contacted together in the solution and form the organometallic phosphine complex required herein. Alternately, the complex may be preformed and introduced into the solution of the nitroalcohol. It is this complex or a material formed via this complex which provides the effective catalyst activity found capable of enhancing the conversion of nitroalcohol to amino alcohol as taught herein. This invention is not meant to be limited by exact nature of the catalytic specie but only by the fact that the specie be formed by or from the presence of the described soluble organometallic phosphine complex.

The solution is contacted with hydrogen gas under a pressure of from about 400 to about 4000 psi, preferably from about 500 to about 1500 psi. The hydrogen gas normally provides all of the pressure and thereby is able to be more effectively solubilized into the solution to achieve the desired reduction.

The process is normally run in a vessel capable of maintaining the above described pressure. This is normally a sealed container. The solution of nitroalcohol and solvent is introduced into the container followed by introduction of the organometallic and organophosphine compounds. The reaction vessel is sealed and pressurized with hydrogen to the desired pressure. The reaction should be carried out at a moderately elevated temperature of from about 30° to about 150° C. with from about 50° to 125° C. being preferred. The temperature and pressure need not be highly elevated but should be sufficient, in combination, to maintain a solution within the reaction vessel.

The resultant amino alcohol can be separated from the reaction media by any conventional method such as by distillation, chromatographically or by other known methods.

The following examples are given for illustrative purposes only and are not meant to be a limitation on the invention as defined by the claims appended hereto.

All parts and percentages are by weight unless otherwise indicated.

EXAMPLE I

A stainless steel autoclave was charged with 3.700 parts 2-nitro-1-butanol, 0.364 part (1,2-bis(diphenylphosphino) propane, 0.269 part [RhCl(NBD)]$_2$, 5 parts EtOH, and 5 parts toluene. It was pressurized to 1000 psi with H$_2$, then heated at 60° C. for 20 hours with stirring. The yield of 2-amino-1-butanol was 78% as determined by GC.

EXAMPLE II

A stainless steel autoclave was charged with 200 parts 2-nitro-1-butanol, 0.322 part PdCl$_2$(PhCN)$_2$, 0.502 part (alpha-[2,1'-bis(diphenylphosphino) ferrocenyl]ethanol, and 5000 parts EtOH. It was pressurized to 1000 psi with H$_2$, then heated at 75° C. with stirring for 18 hours. The yield of 2-amino-1-butanol was 41% as determined by gas chromatography.

EXAMPLE III

A reaction was carried out as described in Example II, above, except using 0.282 part [IrCl(COD)]$_2$ and 0.370 part alpha-[2-diphenylphosphino)-ferrocenyl]-ethyldimethylamine in place of the palladium complex and phosphine of Example II. The yield was 43% as determined by GC.

EXAMPLE IV

A stainless steel autoclave was charged with 3.700 parts 2-nitro-1-butanol, 0.364 part triphenylphosphine, 0.269 part [RhCl(NBD)]$_2$, 5 parts EtOH, and 5 parts toluene. It was pressurized to 1000 psi with H$_2$, then heated at 60° C. for 20 hours with stirring. 2-amino-1-butanol was determined to be a major product.

EXAMPLE V

The process of Example IV above was repeated except that tricyclohexyl phosphine was used as the phosphine compound to form the catalyst complex. The reaction product solution was analyzed by GC which confirmed that 2-amino-1-butanol was a major product.

I claim:

1. A process for providing homogeneous catalytic hydrogenation of nitroalcohols to form amino alcohols comprising hydrogenating an aliphatic nitroalcohol represented by the formula RR'C(OH)—CR''HNO$_2$, wherein each R, R' and R'' independently is selected from hydrogen, alkyl, or substituted alkyl group and said substitution is of hydroxyl, halogen, amino or aryl group, by contacting a solution of the nitroalcohol in an inert solvent with hydrogen at a pressure of from about 500 to about 1500 psi and a temperature of from about 30° to 150° C. in the presence of soluble catalyst complex formed from a soluble organometallic compound of a metal selected from Rh, Ir, Pt or Pd and a soluble organophosphine represented by Z$_3$P or Z$_2$P—Y—PZ$_2$ wherein each Z represents a C$_1$–C$_{12}$ alkyl or an aryl group and Y represents a divalent C$_1$–C$_{12}$ alkyl or aryl group or an organometallic radical of a transition metal, and separating the amino alcohol formed.

2. The process of claim 1 wherein the organometallic compound is a rhodium ligand compound.

3. The process of claim 2 wherein the organometallic compound is a rhodium norbornadiene dihalide.

4. The process of claim 2 wherein the organometallic compound is a rhodium carbonyl halide.

5. The process of claim 1, 2, 3 or 4 wherein the organo phosphine is selected from alpha[2-(diphenylphosphine)-ferrocenyl] ehtyldimethylamine; 2,2-dimethyl-4,5-bis(diphenylphosphinomethyl)-1,3-dioxolane; 1,2-bis (diphenylphosphino) propane; 2,2'-bis(diphenylphosphino-1,1'-binaphthyl; and 2,3-bis(diphenylphosphino) butane.

6. The process of claim 1, 2, 3 or 4 wherein the solvent is slected form a $C_1$–$C_4$ alkanol, benzene or mixtures thereof.

* * * * *